(12) United States Patent
Dykes, Jr.

(10) Patent No.: US 9,568,400 B2
(45) Date of Patent: Feb. 14, 2017

(54) SAMPLING ADAPTER

(75) Inventor: H. Waite H. Dykes, Jr., Huntsville, AL (US)

(73) Assignee: Streamline Automation LLC, Hunstville, AL (US)

( * ) Notice: Subject to any disclaimer, the term of this patent is extended or adjusted under 35 U.S.C. 154(b) by 852 days.

(21) Appl. No.: 13/205,952

(22) Filed: Aug. 9, 2011

(65) Prior Publication Data

US 2013/0036838 A1    Feb. 14, 2013

(51) Int. Cl.
*G01N 1/22*    (2006.01)

(52) U.S. Cl.
CPC ..... *G01N 1/2226* (2013.01); *G01N 2001/2229* (2013.01)

(58) Field of Classification Search
None
See application file for complete search history.

(56) References Cited

U.S. PATENT DOCUMENTS

| | | | | |
|---|---|---|---|---|
| 3,602,629 | A * | 8/1971 | Friedrich et al. | 174/15.3 |
| 4,359,908 | A * | 11/1982 | Perras | 73/863.85 |
| 5,792,423 | A * | 8/1998 | Markelov | 422/83 |
| 6,293,163 | B1 * | 9/2001 | Johnston et al. | 73/864.74 |
| 6,346,586 | B1 * | 2/2002 | Agapiou et al. | 526/160 |
| 6,935,199 | B2 * | 8/2005 | Wickland et al. | 73/864.74 |
| 6,948,391 | B2 * | 9/2005 | Brassell et al. | 73/863.84 |
| 7,374,054 | B2 * | 5/2008 | Brockwell | 215/311 |
| 7,464,614 | B2 * | 12/2008 | Harvey | 73/863.84 |
| 2004/0069076 | A1 * | 4/2004 | Gamble | 73/863.85 |

\* cited by examiner

*Primary Examiner* — Robert R Raevis
(74) *Attorney, Agent, or Firm* — Patent Grove LLC; Tomas Friend

(57) ABSTRACT

A sampling adapter having a tubular body with a first open end and a second open end encloses an adapter volume that is accessible by a sensor probe through a septum in cap covering the first open end. The second open end is configured to be reversibly attachable to an opening in a storage container.

9 Claims, 3 Drawing Sheets

SAMPLING ADAPTER

BACKGROUND OF THE INVENTION

Field of the Invention

The invention is an apparatus and method for sampling a gas in a container.

Description of Related Art

Fifty-five-gallon steel drums and similar containers are used for the transport and storage of a wide variety of materials, including toxic and non-toxic waste from factories, power plants, laboratories, and environmental cleanup sites. In some cases, the contents of a container or group of containers are completely unknown because information about the contents is lost or was never recorded. In some cases the contents of a container, or one or more of a group of containers, may be suspected of containing a toxic substance or material contaminated with a toxic substance. These situations require a means for sampling the contents of a container in order to establish the identity of its contents and/or to establish whether a particular substance or group of substances are present in the container.

A number of apparatus, methods, and systems have been developed to sample the contents of storage and transport containers. These systems usually involve the collection of a small amount of liquid sample from a container or tank followed by the analysis of the collected sample. Gas chromatography (GC) is one of the most common methods used for the analysis of volatile liquids such as organic solvents, gasoline, and other petroleum-based fuels. GC analysis of a sample usually involves placing a solid or liquid sample containing a volatile substance into a sample vial and obtaining gas from the headspace in the sample vial. Regardless of the analytical method used, obtaining a liquid sample suffers from a number of drawbacks, including the transport of a sample container for analysis of its contents, the eventual disposal of unused liquid, and disposal or cleaning of the sample container.

To overcome at least some of the drawbacks associated with the collection of solid and liquid samples, systems have been developed for obtaining gaseous samples for analysis. For example, U.S. Pat. No. 6,935,199 discloses a headspace gas sampling and venting method in which a first punch having a hollow passage containing a filter and a second punch having a septum are inserted through the lid of a container by a pneumatic gun. A needle is used to obtain a sample the headspace gas in the container through the second punch. The first punch provides an inlet allowing air to enter the container as fluid is removed through the second punch. The sample of headspace gas is placed in a canister and shipped for analysis at a remote site. This system eliminates the collection of non-gaseous samples, but retains the drawback of shipping samples for subsequent analysis and introduces the drawback of requiring a pneumatic gun to insert the first and second punches.

WO 97/47728 discloses monitoring the contents of sealed culture bottles by a sensing unit that is fitted to a sealed container. The sensing unit comprises a housing containing a transducer that is responsive to a sensed property of a liquid in the sealed container and provides electrical outputs proportional to the sensed property to a data processing means. This system provides on-site analysis for bottle-sized containers but requires a sensor for each container being monitored.

Portable electro-chemical sensors may be used to detect and measure volatile substances. For example, a volatile organic compound sensor system disclosed in U.S. Pat. No. 7,487,662, which is incorporated by reference in its entirety, may be used to detect and measure a variety of halogenated volatile organic compounds. The portable sensor is equipped with a probe that can be inserted through a septum into a sealed sampling jar. The probe is connected to a pump that draws gas fluid from the jar and delivers it to a sensor configured to detect one or more chemical species. The probe is designed to allow ambient air to enter the sealed sampling jar as fluid is removed through the probe.

In one aspect, the present invention is an adapter that provides a head space of defined volume outside a storage container inside which volatile substances may be in equilibrium with the contents of the storage container. The headspace inside the adapter may be used to detect and/or measure an amount of a volatile substance using one or more portable sensors without removing a liquid or solid sample from the container.

BRIEF SUMMARY OF THE INVENTION

The present invention is an adapter and method for sampling volatile materials in a drum or other storage container. The adapter comprises a tubular body with a predetermined inner volume having a first open end and a second open end. The first open end is covered by a cap comprising a septum and the second open end comprises a means for attaching the adapter to an opening in the container. The adapter may also comprise a means for sealing the second open end and/or a baffle for preventing liquid from splashing from the container into the adapter. A sampling method comprises attaching an adapter to an opening in a top surface of a container. Gas in a headspace in the container is allowed to equilibrate with the inner volume of the adapter, and a probe is inserted through a septum on the adapter. Inserting the probe into the adapter causes or allows the gas inside the adapter to contact a sensor that is in or on the probe or fluidically connected to the probe. The sensor is configured to detect or measure an amount of a volatile substance or combination of volatile substances in the volume of the adapter and thereby detect or measure an amount of a gas or combination of volatile substances in the headspace of the container. The concentration and/or total amount of volatile substance(s) in the liquid may additionally be determined.

DETAILED DESCRIPTION OF THE INVENTION

One embodiment of the sampler adapter configured for use with a 55-gallon drum is used herein for the purpose of describing the invention. The exemplary embodiment is not intended to indicate that this invention is limited to the scope of the embodiment used to describe the invention. The adapter and method may be used with 55-gallon storage containers made of a wide variety of materials including steel, aluminum, glass, polycarbonate, polyethylene, polyvinylchloride, or other polymers/plastics. The sampler adapter may be made of a glass or a suitable plastic material such as polycarbonate, polyethylene, polyvinylchloride, or polypropylene. The storage container may contain any volume of liquid and/or solid. The volume of the storage container is preferably between at least 5 gallons and 5,000 gallons; more preferably between 20 gallons and 2,000 gallons, and most preferably between about 25 gallons and about 500 gallons.

A "tubular" body, as used herein refers to a body having tubular shape with an opening at each end. The tube may be straight, curved, bent, and/or angled and may have a cross-sectional shape that is circular, elliptical, square, triangular, and/or rectangular, for example. The tubular body is preferable a straight tube with a circular cross-section and preferably has openings that are circular in cross-section.

A "septum" as used herein refers to a sheet or disk made of an elastic material that can be pierced by a solid or hollow needle and which reseals itself when the needle is removed. Septa are described, for example in U.S. Pat. No. 4,248,355 and U.S. Pat. No. 4,773,552, which are incorporated by reference in their entirety.

Figure 1:
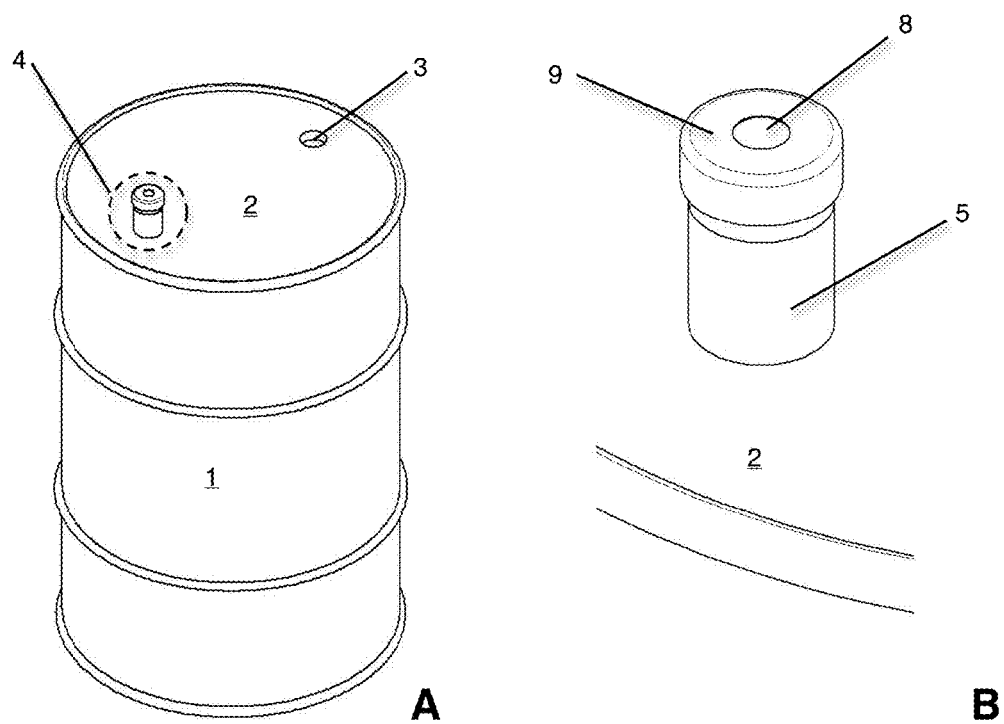
FIGS. 1A and 1B show a perspective view of a drum with a sampling adapter.
Figure 2:
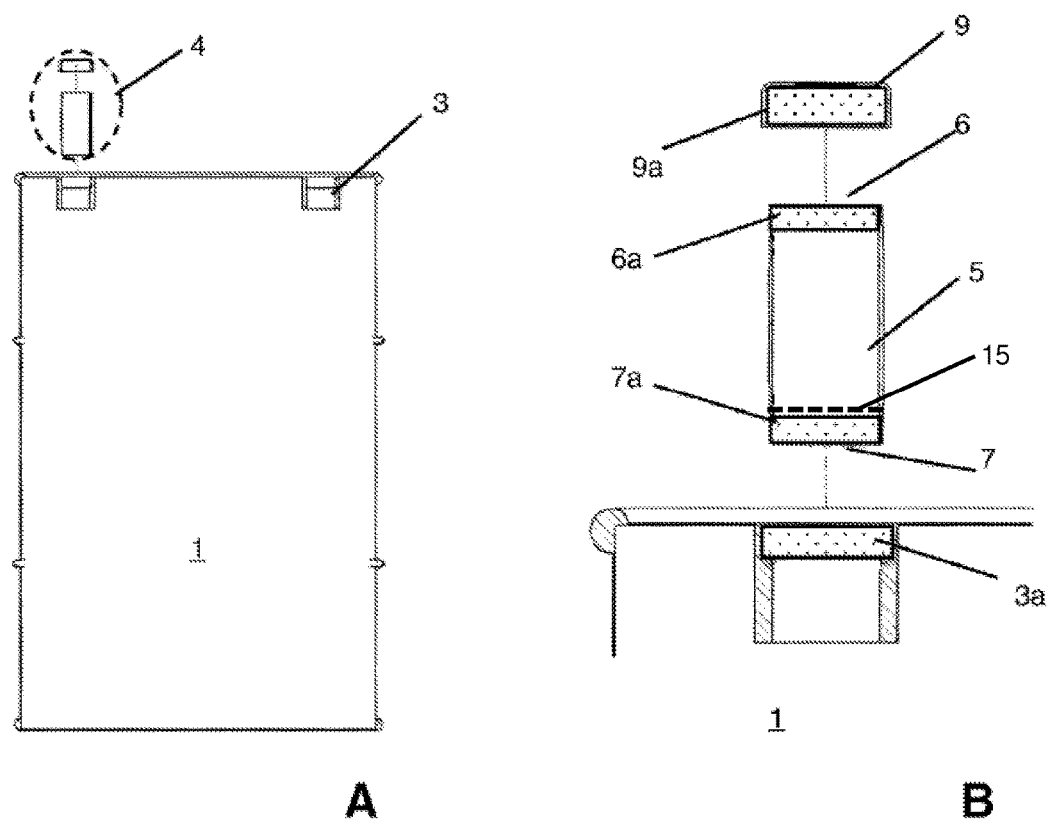
FIGS. 2A and 2B show a cross-section view of a drum with a sampling adapter.

FIG. 1A and FIG. 2A show a storage container 1 having a top surface or lid 2 with two openings 3 and a sampling adapter 4 attached to one of the openings 3. In this example, the storage container is a 55-gallon metal drum. The container 1 may be made of a metal, glass, plastic, or other material and may have a volume larger or smaller than 55 gallons. The top surface or lid 2 may be a permanent or detachable flat lid as shown in FIG. 1A or the lid may be a convex or concave threaded lid or cap, for example. The top surface 2 must have at least one opening 3, a bunghole for example, to which the sampler adapter 4 may be attached.

FIG. 1B and FIG. 2B show a close view of a sampler adapter 4 configured for attachment to a bunghole of a 55-gallon drum. A bunghole is typically configured to have female threads that are used to seal the bunghole using a lid that has male threads. The embodiment of the adapter 4 shown in the figures comprises a tubular body 5 having a first open end 6 and a second open end 7. The first open end 6 is reversibly attachable to a cap 9 through attachment means 6a and 9a on the body and cap. The cap 9 comprises a septum 8, which may be an integral part of the cap or reversibly attached to the cap 9. The second open end 7 of tubular body 5 is reversibly attachable to drum opening 3 through reversible attachment means 3a and 7a on the drum lid 2 and tubular body 5. In the figures, the reversible attachment means 7a and 3a are male and female screw threads, respectively.

Figure 3:
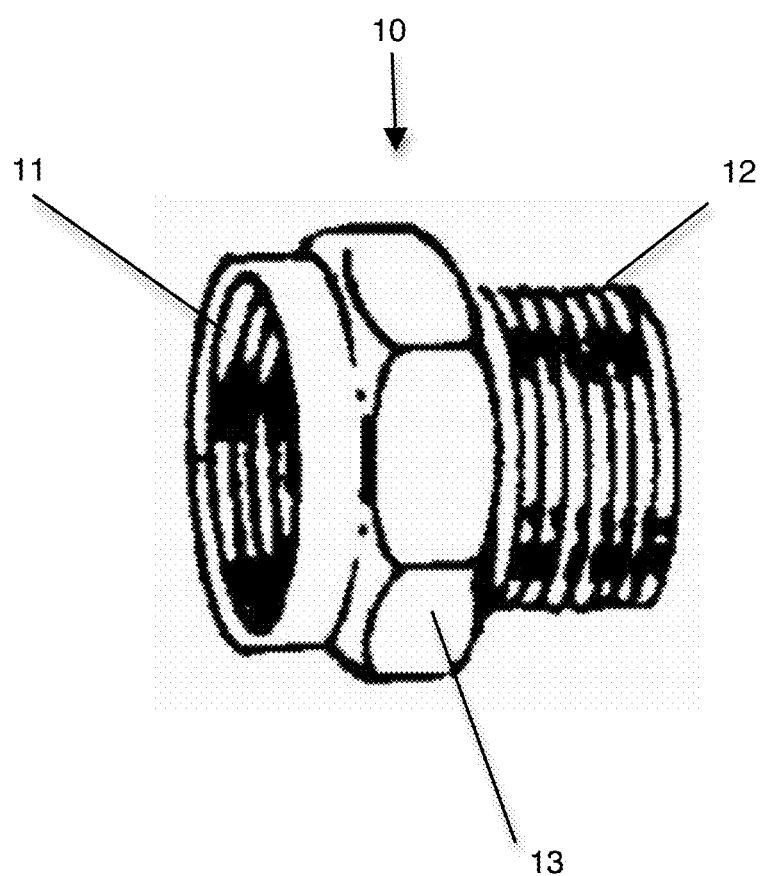
FIG. 3 is a drawing is a plastic connector configured to connect a sampling adapter made from a glass to a drum that is made of a metal.

In a preferred embodiment, the sampling adapter is made of polycarbonate or other hard plastic resistant to most organic solvents and comprises male threads for attachment to a bunghole on a 55-gallon drum. In another preferred embodiment, the sampling adapter is made of a glass and is configured for attachment to a metal storage container though a plastic connector 10 (FIG. 3). The connector 10 comprises male threads for attachment to a bunghole of a metal drum and female threads for attachment to the sampling adapter. The connector may also comprise a grippable or tool-fitting surface 13 configured to allow the connector to be tightened onto or loosened from a bunghole. In some embodiments, the sampler adapter may be made from a glass or a plastic that is nontransparent to infrared, visible, ultraviolet, and/or other wavelength ranges to prevent decomposition or other chemical reactions from taking place in the adapter. An outer surface of the sampling adapter may be modified or covered with a material to facilitate the marking of the adapter using a writing instrument or for the attachment of a label. The sampling adapter may also be equipped with read-only or programmable radio-label chip identifying the adapter to facilitate automated collection of data and association of chemical measurements with corresponding sampling adapters. A chemical sensor used to sample the contents of the sampling adapter may be equipped with a chip reader to collect information associated with a specific sampling adapter or group of adapters. In some instances, the sampling adapter may be irreversibly attached to a container to prevent removal of the adapter and thereby ensure permanent association between a sampling adapter and the storage container it is attached to.

The tubular body 5 contains a specified volume to facilitate the calculation of gas amount or concentration detected or measured in the tubular body and the storage container. The volume contained by the tubular body may be, for example, 125 ml, 250 ml, or 500 ml. The cap 9 comprising a septum 8 may be an integral part of the adapter 4 and/or permanently attached to the first end 6 of the tubular body 5 or the cap may be reversibly attached to the tubular body by attaching means 6a, 9a. By way of example, the cap may be in the form of a screw-on cap having a central opening containing a septum and configured to form a gas-tight seal when screwed onto the first open end 6 of the tubular body 5. The cap may be in the form of a stopper having an opening containing a septum. Other attachment means such a clips, snaps, compression clamps, c-clamps, elastic tubing, or elastic tape may also be used. The second open end 7 of the tubular body 5 may be reversibly attached to opening 3 to form a gas-tight seal by any of a variety of reversible attachment means such as clips, clamps, elastic tubing or elastic tape. A baffle 15 may optionally be located near the second opening 7 to prevent liquid from splashing into the adapter body from the storage container. The baffle may be, for example, a mesh made of plastic or metal or a series of overlapping plates.

To detect or measure an amount of a gas or combination of gasses in the sampler adapter, the second open end 7 of the tubular body 5 is attached to an opening 3 in a storage container in a reversible and gas tight manner. The first open end 6 of the tubular body may be covered by a cap 9 comprising a septum 8 or, if it is not covered, a cap 9 comprising a septum 8 is reversibly attached to the first open end. The capped adapter remains reversibly attached to the opening in the container for a predetermined period of time to allow the concentrations of gas(ses) in a headspace inside the storage container and the volume of the tubular body 5 to equilibrate. The time allowed for equilibration may be, for example, 0.25 hr, 0.5 hr, 1 hr, or 2 hrs. At the end of the predetermined time or some time thereafter, a probe is inserted through the septum 8 and into the volume of the tubular body 5 to detect or measure an amount or concentration of a gas or group of gasses in the volume of the tubular body 5.

By way of example, the probe may be a specially adapted hollow needle used with an HVOC detector. The hollow needle is in fluid communication with a sensor configured to detect or measure a concentration of halogenated hydrocarbons and a pump that drawn gas into the hollow needle from the volume of the tubular body and across the sensor, which is located in a housing. The hollow needle is adapted with an opening that allows ambient air to enter the volume inside the tubular body and thereby prevent the formation of a negative backpressure.

The probe inserted through the septum 8 and into the volume of the tubular body 5 may comprise a sensor that is brought into contact with the gas inside the tubular body 5.

Examples of such sensors include integrated microchip chemical sensors as described in U.S. Pat. No. 5,822,473 and modular fiber optic chemical sensors as described in U.S. Pat. No. 4,824,206.

Dimensions for the tubular adapter body 5 may be selected to accommodate probes of various lengths.

Reference to particular embodiments of the present invention have been made for the purpose of describing the sampler adapter and method. It is not intended that such references be construed as limitations upon the scope of this invention except as set forth in the following claims.

What is claimed is:

1. An adapter for sampling one or more volatile substances in an airtight storage container, said adapter comprising:
    a tubular body having a first open end and a second open end and enclosing an adapter volume and a cap covering the first open end, said cap comprising a septum;
    wherein the second open end is configured to be reversibly attachable to an existing opening in said storage container in a gas-tight manner by a means of a reversible attachment such that a concentration of a gas in a headspace inside the storage container may equilibrate with the adapter volume of the tubular body outside the headspace and wherein the storage container contains a volume of at least 5 gallons, wherein the adapter volume is selected from the group consisting of 125 ml, 250 ml, and 500 ml.

2. An adapter for sampling one or more volatile substances in an airtight storage container, said adapter comprising:
    a tubular body having a first open end and a second open end and enclosing an adapter volume and a cap covering the first open end, said cap comprising a septum;
    wherein the second open end is configured to be reversibly attachable to an existing opening in said storage container in a gas-tight manner by a means of a reversible attachment such that a concentration of a gas in a headspace inside the storage container may equilibrate with the adapter volume of the tubular body outside the headspace and wherein the storage container contains a volume of at least 5 gallons, wherein the tubular body of sampling adapter is made of a glass or a plastic selected from the group consisting of polycarbonate, polyethylene, polyvinylchloride, or polypropylene.

3. A method for sampling the volatile contents in a container comprising the steps of:
    providing a sampling adapter, comprising a tubular body having a first open end and a second open end and enclosing an adapter volume and a cap covering the first open end, said cap comprising a septum, wherein the second open end is configured to be reversibly attachable to an existing opening in said storage container in a gas-tight manner by a means of a reversible attachment such that a concentration of a gas in a headspace inside the storage container may equilibrate with the adapter volume of the tubular body outside the headspace and wherein the storage container contains a volume of at least 5 gallons
    attaching the sampling adapter to an opening in the container in an air-tight and reversible manner;
    after a predetermined period of time, inserting a probe through the septum of the sampling adapter and into the volume of the tubular body but not into the volume of the storage container to detect or measure an amount or concentration of a gas or group of gasses in the volume of the tubular body; and
    removing the probe from the tubular body of the sampling adapter.

4. The method of claim 3, wherein the predetermined period of time is sufficient to allow the concentrations of gases in a headspace inside the storage container and the volume of the tubular body to equilibrate.

5. The method of claim 3, wherein the predetermined period of time is between 0.25 hours and 2 hours.

6. The method of claim 3, wherein the probe is a hollow needle in fluid communication with a sensor outside the probe and a pump is used to draw a sample of gas from inside the sampling adapter to the sensor.

7. The method of claim 3, wherein the probe comprises a sensor configured to detect or measure a concentration of gas inside the sampling adapter.

8. The method of claim 3, wherein the storage container is a 55-gallon drum and the opening in the storage container is a bunghole.

9. An adapter for sampling one or more volatile substances in an airtight storage container, said adapter comprising:
    a tubular body having a first open end and a second open end and enclosing an adapter volume and a cap covering the first open end, said cap comprising a septum;
    wherein the second open end is configured to be reversibly attachable to an existing opening in said storage container in a gas-tight manner by a means of a reversible attachment such that a concentration of a gas in a headspace inside the storage container may equilibrate with the adapter volume of the tubular body outside the headspace and wherein the storage container contains a volume of at least 5 gallons, wherein the storage container is a 55-gallon drum, the opening in the storage container is a bunghole, and the second open end is configured to reversibly attach to the bunghole.

* * * * *